United States Patent [19]
Samuels

[11] Patent Number: 5,947,995
[45] Date of Patent: Sep. 7, 1999

[54] METHOD AND APPARATUS FOR REMOVING BLOOD CLOTS AND OTHER OBJECTS

[76] Inventor: Shaun Lawrence Wilkie Samuels, 1055 Sonoma Ave., Menlo Park, Calif. 94025

[21] Appl. No.: 09/129,906

[22] Filed: Aug. 6, 1998

Related U.S. Application Data

[63] Continuation-in-part of application No. 08/871,877, Jun. 6, 1997, Pat. No. 5,848,964.

[51] Int. Cl.[6] .................................................. A61M 29/00
[52] U.S. Cl. .......................................................... 606/200
[58] Field of Search .................................... 606/200, 159, 606/151, 194; 604/96

[56] References Cited

U.S. PATENT DOCUMENTS

| | | | |
|---|---|---|---|
| 5,053,008 | 10/1991 | Bajaj | 606/200 |
| 5,769,816 | 6/1998 | Barbut et al. | 606/200 |
| 5,814,064 | 9/1998 | Daniel et al. | 606/200 |
| 5,827,324 | 10/1998 | Cassell et al. | 606/200 |

*Primary Examiner*—Michael Buiz
*Assistant Examiner*—Kevin Truong
*Attorney, Agent, or Firm*—Rudnick & Wolfe

[57] ABSTRACT

A catheter has a central lumen so that it may be positioned by a guidewire within a tubular structure of the human body. The catheter has attached to its distal end an inflatable cuff featuring an inflation space with a ring-like cross section. A pouch is circumferentially attached to the cuff The catheter features an inflation lumen that is in communication with the inflatable cuff. The proximal port of the inflation lumen receives a syringe so that the cuff may be inflated when the cuff and pouch are positioned within a tubular structure. A filament passes through the inflation space of the cuff and the inflation lumen and exits the proximal port of the inflation lumen. As a result, the cuff may be cinched so that the pouch is closed in a purse-string fashion to capture an object in the tubular structure. The object may then be removed from the patient's body.

22 Claims, 7 Drawing Sheets

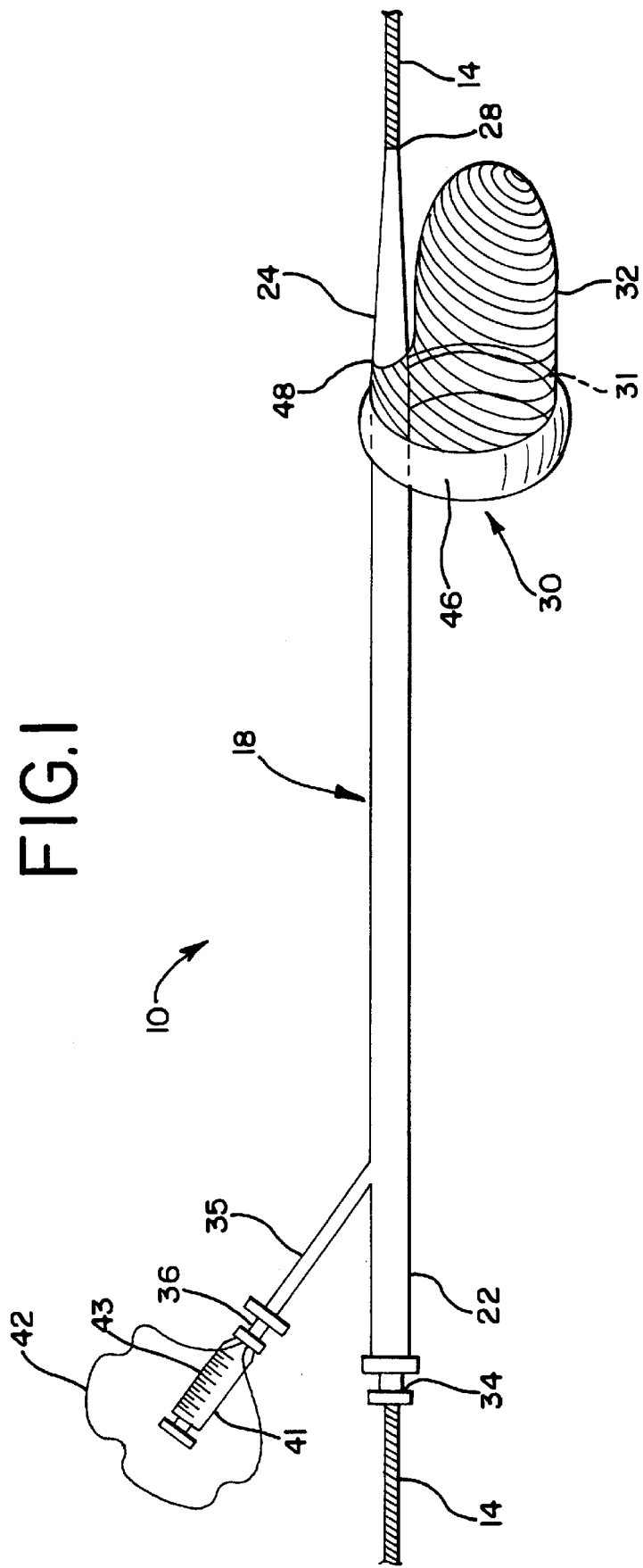

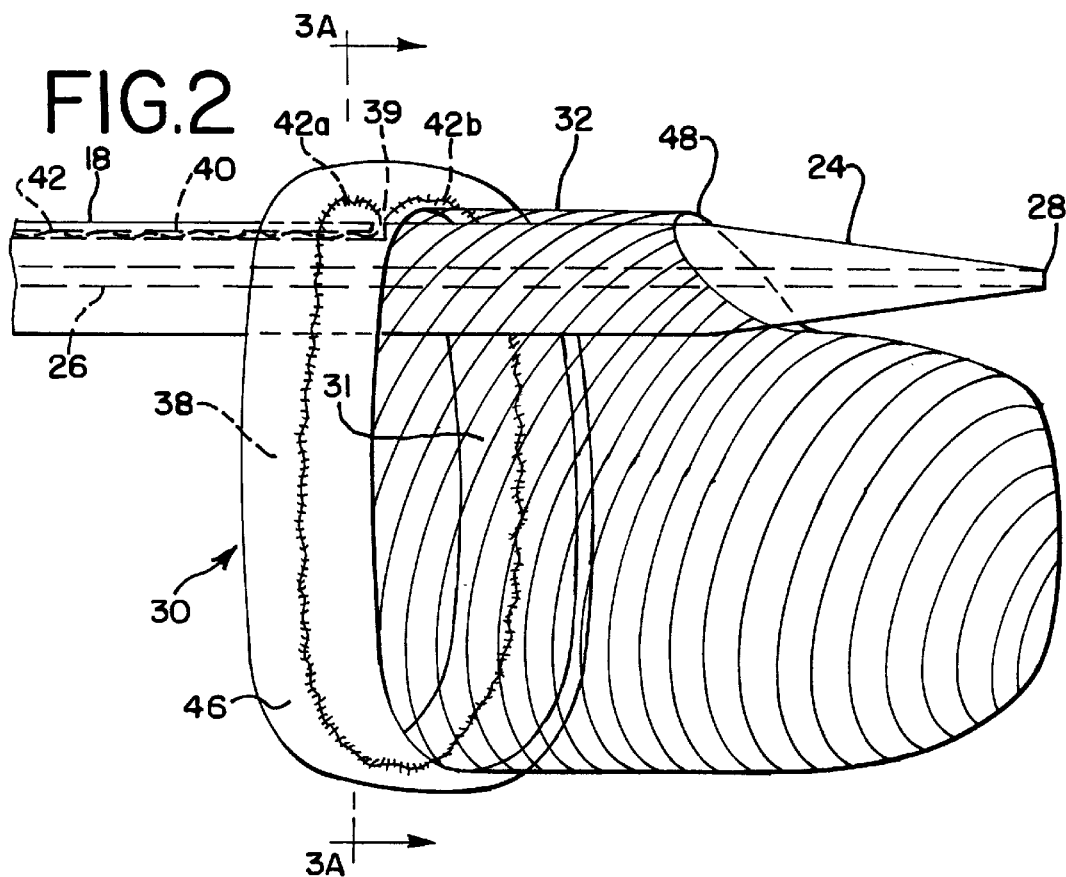
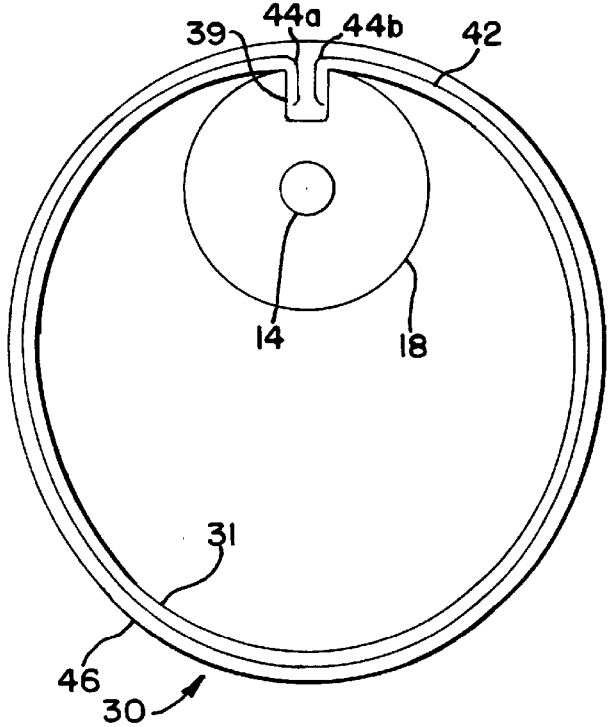

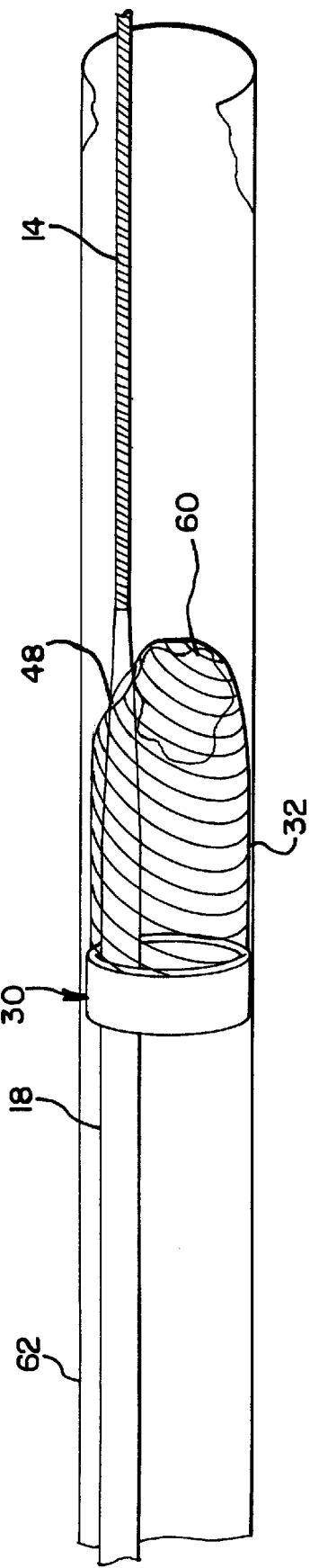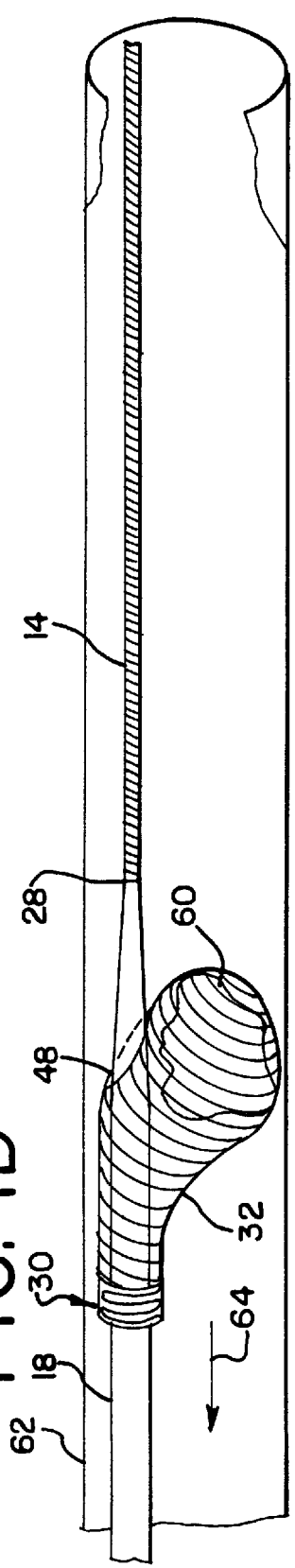

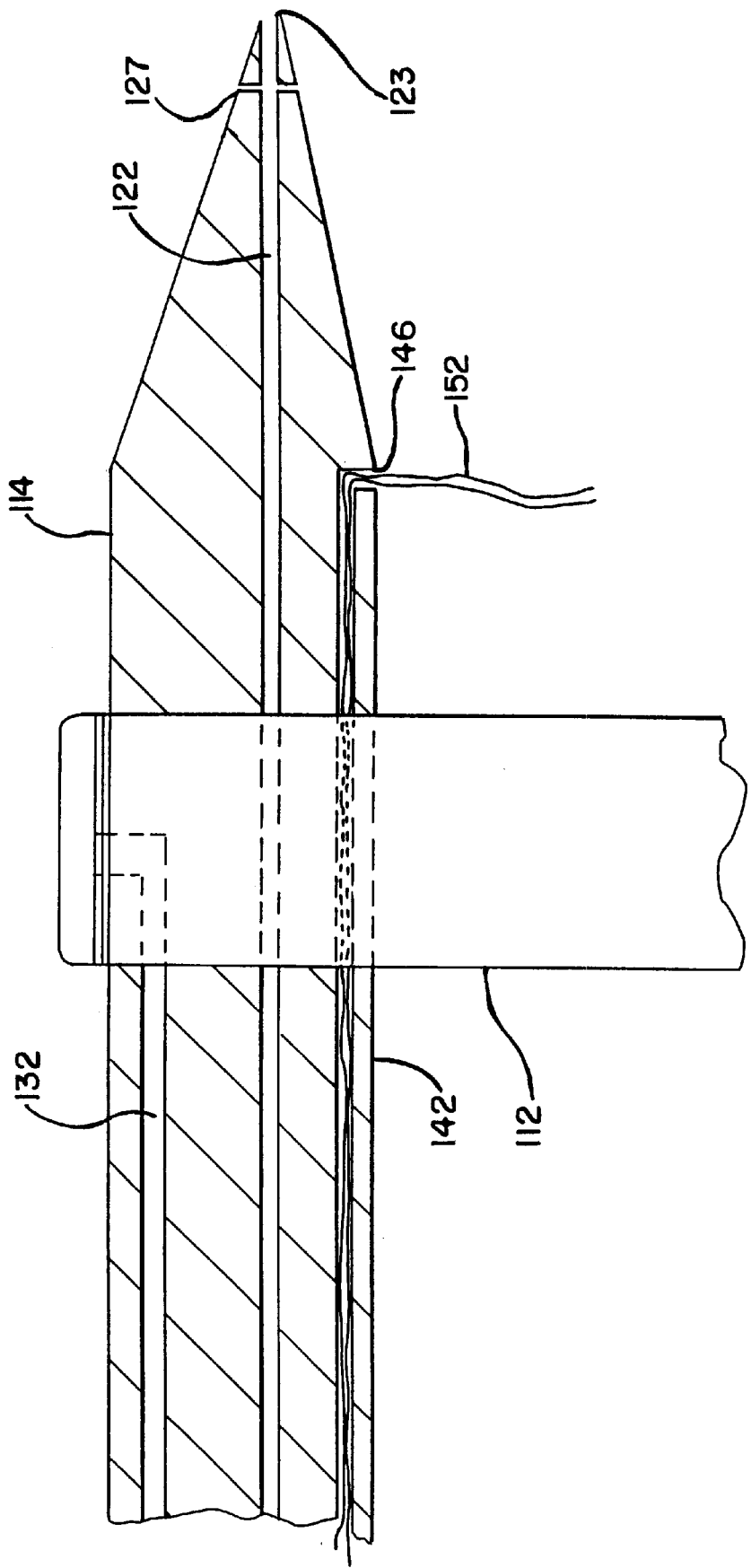

1

METHOD AND APPARATUS FOR REMOVING BLOOD CLOTS AND OTHER OBJECTS

CROSS REFERENCE TO RELATED APPLICATION

This application is a continuation-in-part of U.S. application Ser. No. 08/871,877 filed Jun. 6, 1997 now U.S. Pat. No. 5,848,964.

BACKGROUND OF THE INVENTION

Many medical procedures involve the removal of undesirable material from various tubular structures within the human body. Such materials may be of the body's origin or man-made. Examples include, but are not limited to, blood clots in the arteries and veins, foreign bodies introduced by surgery that have migrated or become dysfunctional and stones in the biliary or urinary systems. While these unwanted objects may be removed by surgical procedures, interventional radiological techniques have been developed to provide a less-invasive alternative.

One type of interventional radiological technique involves the use of a snaring device that is introduced into the tubular structure by a catheter or sheath and positioned by a guidewire with endoscopic or fluoroscopic guidance. The snaring devices commonly feature a wire cage-like structure positioned upon their distal end portions that may be flexed to receive the target object. Once the snaring device is in position, it is operated remotely by the physician to capture, and in some instances crush, the target object. The object may then be withdrawn from the body through the catheter or sheath insertion site or left to be ultimately washed out of the body by normal body fluids. Examples of such devices are presented in U.S. Pat. No. 4,198,960 to Utsugi, U.S. Pat. No. 4,927,426 to Dretler and U.S. Pat. No. 5,496,330 to Bates et al.

While such devices are effective, they do not feature a means for affirmatively trapping an object. As a result, there is always a danger that an object will become unintentionally dislodged from the snare prior to its removal. The object would then be free to migrate through the tubular structure which could cause severe medical complications.

Other methods of removing objects from the tubular structures of the body vary considerably depending upon the specific object to be removed and the tubular structure involved. For example, a medication may be injected into a vein or artery in an attempt to dissolve a blood clot. Examples of suitable medications include urokinase, streptokinase, t-PA, etc., with or without a blood plasma or saline carrier. U.S. Pat. No. 4,692,139 to Stiles discloses a catheter suitable for performing such a procedure.

While effective, the infusion of such medications has associated risks. More specifically, there may be a precipitation of bleeding at the catheter insertion site or in the stomach or brain. Furthermore, such medications are extremely costly and a great deal often is often consumed during their administration in that the patent must be closely monitored for complications.

As disclosed by U.S. Pat. No. 5,092,839 to Kipperman, a balloon catheter may be used to remove thrombus and plague from a coronary artery. The '839 patent discloses a device featuring a balloon catheter disposed through the lumen of a guide catheter, the latter of which features an expandable distal tip. Once the device is positioned in the artery, the balloon is inflated to expand the distal tip of the guide catheter. The balloon is then deflated and the distal tip of the guide catheter retains its expanded shape. The balloon catheter is then extended out from the distal tip and beyond the occluded portion of the artery and is once again inflated. The inflated balloon is then retracted back into the guide catheter, carrying with it residual pieces of thrombus and/or plaque which has been dislodged from the artery wall.

A disadvantage of the apparatus and method of the '829 patent, however, is that, in order to properly expand the distal tip of the guide catheter, the balloon must be precisely positioned. Furthermore, once the distal tip of the guide catheter is expanded, it cannot be contracted. As a result, the physician faces increased difficulty when attempting to remove the distal tip from the body.

For the removal of stones from the biliary or urinary systems, lithotripsy devices have been developed. As described in U.S. Pat. No. 4,957,099 to Hassler and U.S. Pat. No. 5,658,239 to Delmenico, these devices propogate shock waves through a fluid medium and into the patient's body so that stones are pulverized. Although effective, lithotripsy devices are expensive, complex and cumbersome.

Patients who are temporarily immobilized because of recent surgery or trauma face an increased risk of blood clot formation in the veins of the legs. As a result, in such situations, it is desirable to filter the inferior vena cava, that is, the main vein draining the abdomen and lower extremities of the body, to prevent the migration of these blood clots.

Examples of existing vena cava filters are presented in U.S. Pat. Nos. 4,619,246 to Molgaard-Nielson et al., 5,133, 733 to Rasmussen et al. and 5,397,310 to Chu et al. Filters of the type disclosed by these patents all are anchored to the interior wall of the vena cava by way of metal hooks or legs. As a result, it is difficult, if not impossible, to remove such devices from the vena cava without causing severe damage to the vena cava's interior wall.

It follows that such devices must be permanently placed in the inferior vena cava without the option for retrieval even though a patient's period of risk may be limited. Health care providers using these devices thus are often faced with the difficult decision whether to permanently implant a device, even though the period of risk is limited, or, alternatively, to allow the patient to be at risk of the occurrence of a potentially fatal event. Furthermore, in the case of patients with recent trauma or planned surgery, the absence of clotting may be inaccurately indicated. As a result, the health care provider will often decide against inserting a permanent device, and hence the patient is exposed to risk.

In response to this problem, devices for temporary inferior vena cava filtration have been developed. Examples of such a device is disclosed in U.S. Pat. Nos. 5,329,942 to Gunther et al. and 4,662,885 to DiPisa. Like the vena cava filters discussed above, however, the filters of the '942 and '885 patents do not provide a means for temporarily adjusting the size of the filter opening once the filter is positioned within the vessel. Such a feature would be invaluable in allowing the devices to be used to retrieve trapped clots.

Finally, U.S. Pat. No. 5,423,851 to Samuels discloses an apparatus employing an inflatable cuff to secure an endoluminal device, such as a filter, within a tubular structure of the body. This apparatus, however, is designed for permanent placement of devices within tubular structures via radially projecting barbs and thus is not well-suited to removing objects from the body.

Accordingly, it is an object of the present invention to provide a method and apparatus for removing objects from tubular structures of the body that is minimally invasive.

It is another object of the present invention to provide a method and apparatus for definitively trapping objects in tubular structures of the body.

It is another object of the present invention to provide a method and apparatus for removing objects from tubular structures of the body that does not require the use of medications.

It is still another object of the present invention to provide a method and apparatus for removing objects from tubular structures of the body that may be expanded after insertion and retracted prior to removal.

It is still another object of the present invention to provide a method and apparatus for removing objects from tubular structures that does not require expensive, complex or cumbersome equipment.

SUMMARY OF THE INVENTION

The present invention is directed to a method and apparatus for removing objects from tubular structures in the human body. The device features a catheter having a proximal portion and a distal portion. A central lumen extends coaxially with the longitudinal axis of the catheter so that the catheter may travel along a guidewire. An inflation lumen also extends longitudinally through the catheter and features ports through the catheter proximal and distal portions. The distal port of the inflation lumen is in communication with an inflatable cuff while the proximal port is connected to a means for inflating the cuff with inflation material. The inflatable cuff contains an inflation space having a generally ring-like cross section. A pouch is attached to the circumference of the cuff. The pouch may be porous or non-porous. A filament is positioned through the inflation lumen and the inflation space of the cuff. The filament exits the inflation lumen port in the proximal portion of the catheter.

In operation, the deflated cuff and pouch are wrapped about the catheter as it is introduced into a tubular structure of the body. The cuff and pouch are positioned beyond the object to be removed. The cuff is then inflated so that the pouch spans the interior of the tubular structure. The catheter is then moved so that the object is received in the pouch. The physician then tightens the filament so that the pouch is closed in a purse-string fashion. This allows the object to be captured within the pouch which the physician then removes from the tubular structure and the patient's body.

The following detailed description of embodiments of the invention, taken in conjunction with the appended claims and accompanying drawings, provide a more complete understanding of the nature and scope of the invention.

BRIEF DESCRIPTION OF THE DRAWINGS

FIG. 1 is a perspective view of an embodiment of the device of the present invention with the inflatable cuff in an inflated condition;

FIG. 2 is a cross-sectional perspective view of the catheter of FIG. 1 taken down its longitudinal axis with a partial sectional perspective view of the pouch and cuff, the latter of which is in an inflated condition;

FIGS. 3A and 3B are cross-sectional views of the catheter and cuff of FIG. 2 taken along line 3—3 with the cuff in inflated and deflated conditions, respectively;

FIGS. 4A through 4D show in cross-section a tubular structure of the human body with a side elevation view of the device of FIG. 1 being deployed therein in accordance with the method of the present invention;

FIG. 6 is a cross-sectional view of the catheter of the vena cava filter device of FIG. 5 taken down its longitudinal axis;

DESCRIPTION OF THE PREFERRED EMBODIMENTS

Figure 4A:
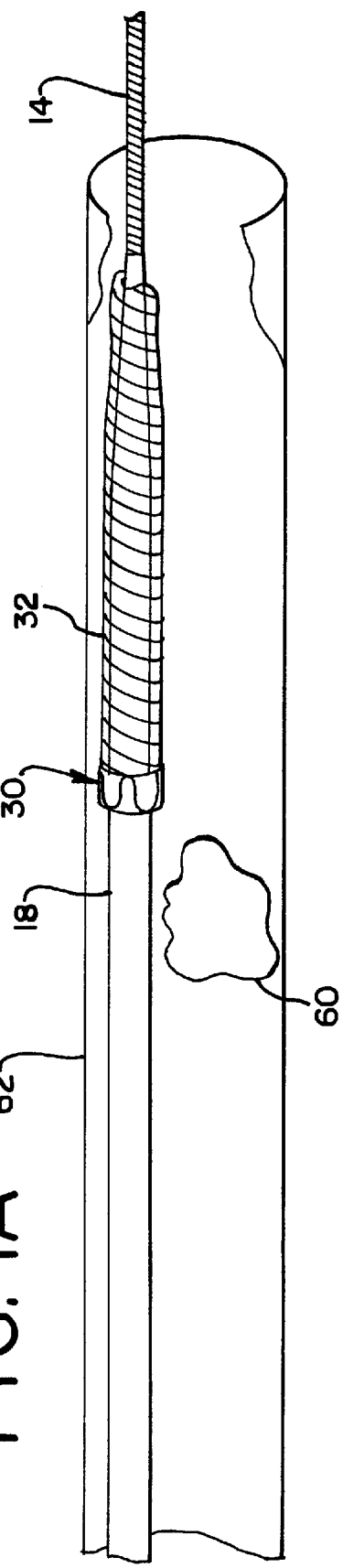

Referring to FIG. 1, an embodiment of the apparatus of the present invention, placed over a guidewire 14 and in its inflated and deployed configuration, is indicated generally at 10. The device features a catheter, indicated generally at 18, with proximal portion 22 and distal portion 24. Catheter 18 is preferably constructed of a polymeric plastic which is bioinert. The distal portion 24 tapers down to a distal port or opening 28. This allows catheter 18, as it slides along guidewire 14, to be more easily positioned within tubular structures of the human body.

An inflatable cuff, indicated generally at 30, is attached at its inner surface to the distal portion 24 of catheter 18 via bonding, welding or adhesive. Cuff 30 is composed of a biocompatible, non-thrombogenic polymer plastic such as polyethylene and is of a cylindrical shape with a comparatively large central opening surrounded by the relatively thin inflatable element. As a result, the inflatable element has a ring-like inflation space 38 (FIG. 2). Cuff 30, when inflated, features a profile that creates a minimal impediment to fluid flow through the tubular structure. Cuff 30 may be constructed in a variety of diameters, depending on the size of the tubular structure in which it is positioned and the specific task for which it is intended.

Circumferentially attached to cuff 30 is a pouch 32. Pouch 32 is constructed of a biocompatible, non-thrombogenic polymer plastic that may be porous or non-porous. It preferably is attached to cuff 30 by a biologically inert adhesive. Pouch 32 features a generally conical shape and its diameter and length may be varied depending on the requirements of the procedure.

The proximal portion 22 of catheter 18 terminates in a port 34 preferably having a Luer-lock fitting. In addition, a side-arm port 35 joins proximal portion 22. Both the angle, with respect to catheter 18, and length of side-arm port 35 may be variable. During manufacture, side-arm port 35 and catheter 18 may be molded from a single piece or, alternatively, side-arm port 35 may be bonded to catheter 18. Side-arm port 35 preferably includes a Luer-lock fitting 36.

Turning to FIG. 2, catheter 18 features central lumen 26 and inflation lumen 40. Central lumen 26 is positioned coaxially with the longitudinal axis of catheter 18 and receives guidewire 14. Central lumen 26 is of sufficient size to accommodate a guidewire of at least 0.035 inches in diameter. The Luer-lock fitting of port 34 (FIG. 1) remains outside of the patient's body when the device is in use and accepts a standard syringe so that fluids or medication may be injected when guidewire 14 is removed.

Inflation lumen 40 is disposed generally parallel to central lumen 26 and is communication via port or orifice 39 with inflation space 38 of cuff 30. Referring to FIG. 1, the opposite end of inflation lumen 40 passes through side-arm port 35 and is in communication with the Luer-lock fitting 36. A standard syringe 41 may be attached to the Luer-lock fitting 36 and used to inflate cuff 30 with inflation material. Cuff 30 may also be deflated by syringe 41. Inflation lumen 40 may be of any size that allows cuff 30 to be easily inflated or deflated and is generally of consistent diameter throughout the length of catheter 18.

The inflation material for the cuff may be any biocompatable, non-viscous fluid which may be easily introduced and withdrawn in the aforementioned fashion. In the preferred embodiment, the fluid introduced into cuff 30 is a mixture of saline solution and radio-opaque contrast media so that cuff 30 may be easily visualized under fluoroscopy, the generally accepted imaging technique used in the placement of such intraluminal devices. The radio-opaque contrast, it should be noted, is designed for intravenous injection, and may also be well seen under other imaging techniques such as plain film radiography, computed tomography (CT) and magnetic resonance imaging (MRI).

As shown in FIG. 2, inflation lumen 40, in addition to conducting inflation fluid to cuff 30, contains a filament-like drawstring 42. Filament drawstring 42 may be composed of any biocompatible, high tensile strength material such as polymer plastic, metal or silk. As indicated at 42a and 42b in FIGS. 2 and 3A, upon exiting the distal end of inflation lumen 40, drawstring 42 passes circumferentially through the inflation space 38 so as to create a purse-string type closure mechanism for pouch 32. As shown in FIG. 1, the portion of drawstring 42 extending out of side-arm port 35 and Luer-lock fitting 36 preferably forms a loop. The extremely thin construction of drawstring 42 prevents it from interfering with the connection of syringe 41 to the Luer-lock fitting 36.

In the preferred embodiments shown, port or orifice 39 is positioned through the top surface of catheter 18 so as to join with the inner surface 31 of cuff 30. This allows the outer surface 46 of cuff 30 to be disposed along the interior wall of the tubular structure within which it is positioned without the imposition of catheter 18.

As shown in FIG. 2, the preferred embodiment of pouch 32 features an aperture 48 through which catheter 18 may pass. As a result, pouch 32 may have complete circumferential adhesion to cuff 30. Alternatively, aperture 48 may be eliminated so that cuff 30 and pouch 32 is are not joined in the vicinity of the junction between catheter 18 and cuff 30.

FIGS. 4A through 4D illustrate the steps involved in using the apparatus of the present invention to remove an object 60 from a tubular structure 62 of the human body. Initially, catheter 18, with pouch 32 and deflated cuff 30 wrapped around it, is loaded over a previously placed guidewire 14 and inserted into the tubular structure 62 via the catheter insertion or access site. The catheter insertion site is essentially an incision into the patient's skin and a wall of the desired tubular structure. An introducer sheath (not shown) may optionally be used to assist in the insertion of catheter 18 into the tubular structure 62 and its withdrawal. The wrapped configuration of pouch 32, cuff 30 and catheter 18 allows the components to feature a small profile so that the size of the incision forming the catheter access site may be minimal.

As shown in FIG. 4A, catheter 18 is initially positioned with cuff 30 and pouch 32 beyond the object 60. The length of catheter 18 is such that its distal portion 22 (FIG. 1) and side-arm port 35 remain outside of the patient's body.

Figure 4B:
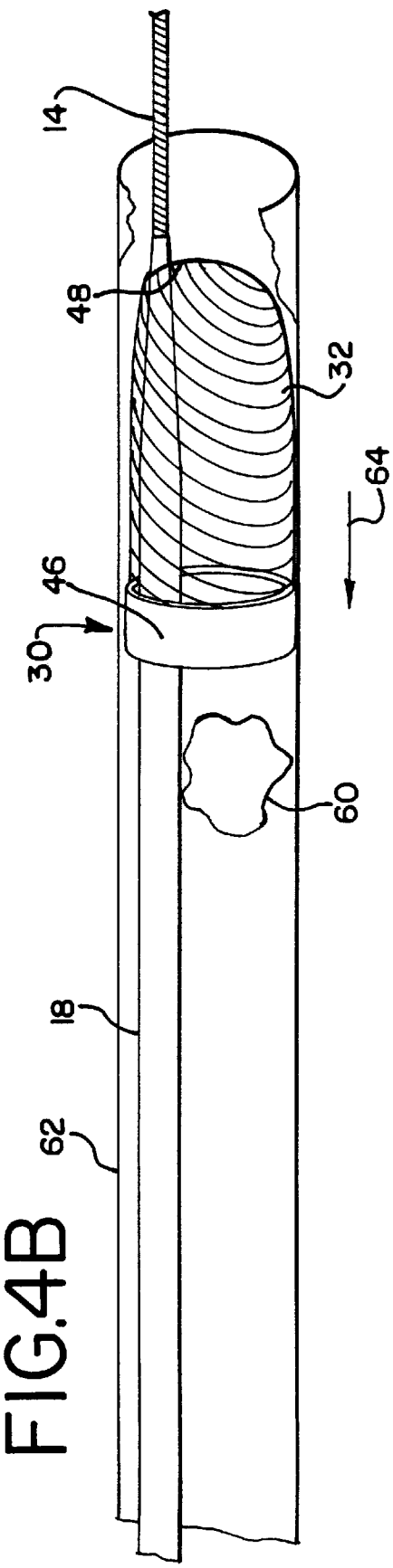

Once catheter 18 is in the position illustrated in FIG. 4A, inflation fluid is injected into cuff 30, via syringe 41 (FIG. 1), through the Luer-lock fitting 36 of side-arm port 35 and inflation lumen 40 (FIG. 2). As a result, as illustrated in FIG. 4B, cuff 30 is inflated with its outer surface 46 disposed against the interior wall of tubular structure 62 and pouch 32 is unwrapped from catheter 18. The contact between outer surface 46 and the interior surface of tubular structure 62 allows cuff 30 to break object 60 free should it be attached to the tubular structure.

Next, catheter 18 is pulled by the physician in the direction indicated by arrow 64 in FIG. 4B. As a result, as indicated in FIG. 4C, the object 60 is captured within pouch 32. Once the object 60 is captured within pouch 32, cuff 30 is deflated and the portion of drawstring 42 exiting the Luer-lock fitting 36 is pulled. The resulting tension on drawstring 42 causes the cuff to cinch about catheter 18 in a purse-string fashion, as illustrated in FIGS. 4D and 3B. As a result, object 60 is trapped within pouch 32 for easy removal from the patient's body, along with catheter 18, through the catheter insertion site.

Figure 5:
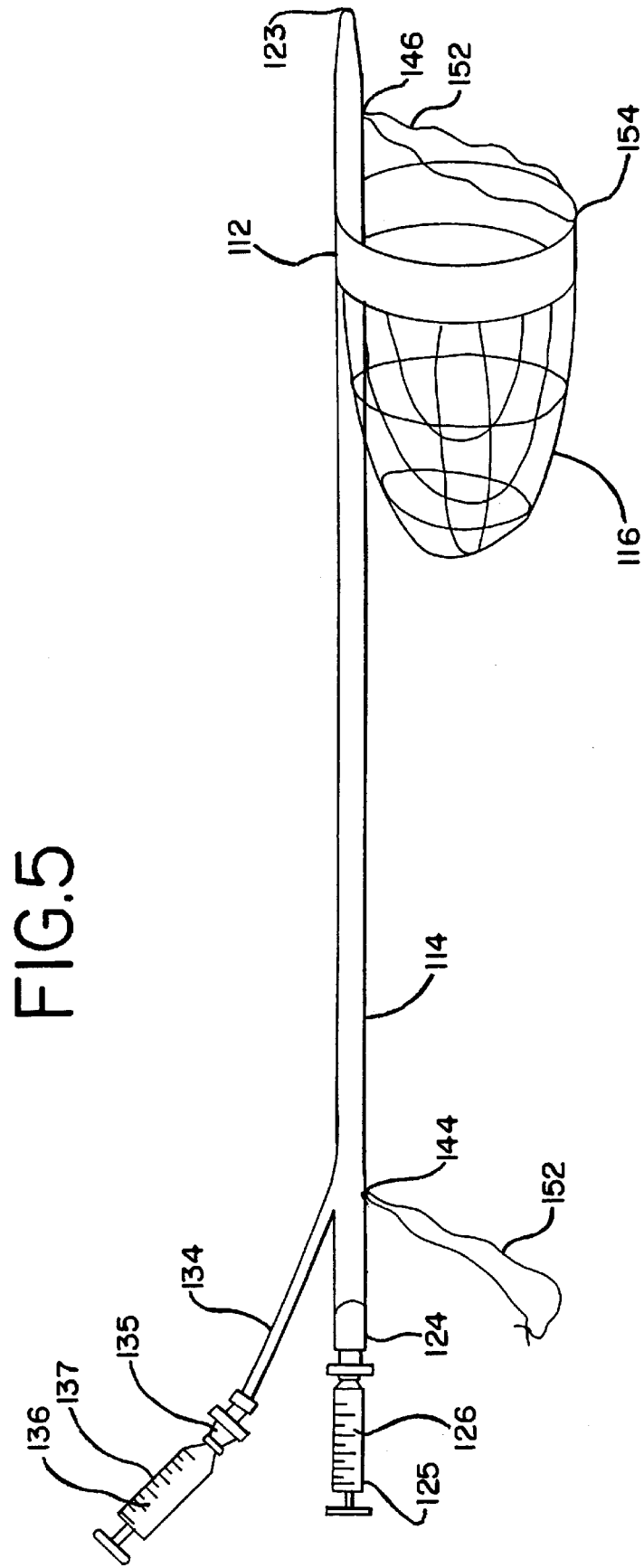
FIG. 5 is a perspective view of a vena cava filter device with its inflatable cuff in an inflated condition.

Referring to FIG. 5, a temporary inflatable vena cava filter device is shown. This device, and its method of use, are disclosed in the commonly assigned U.S. parent application (Ser. No. 08/871,877). The device, shown in its inflated and deployed configuration features an inflatable cuff 112 attached by its inner surface to a catheter, indicated at 114. Also connected about the inner surface of cuff 112 is a porous pouch or a mesh filter 116. Cuff 112 features a construction that is substantially the same as cuff 30 of FIGS. 1 through 4. The cuff diameter is preferably approximately equal to that of the normal human inferior vena cava. Filter 116 features mesh netting which may be constructed of either plastic or metallic strands or similar material. As with pouch 32 of FIGS. 1 through 4, filter 116 is preferably secured to the circumference of the inner surface of cuff 112 by a biologically inert adhesive.

As shown in FIG. 6, a central lumen 122 passes through the longitudinal axis of catheter 114. Central lumen 122 is similar in construction to, and serves the same purposes as, the central lumen 26 of FIG. 2. Preferably, a series of small side-holes, indicated a 127 in FIG. 2, leading from central lumen 122 to the surface of catheter 114 are disposed through tip 123. The presence of side-holes 127 allows for easier passage of fluids through the catheter, and makes it less likely that the central lumen will be occluded by clots, deposits or by contact with the vessel wall. As shown in FIG. 5, a port 124, which is in communication with the central lumen, accepts a standard syringe 125 so that medication 126 may be injected into the blood vessel after removal of the guidewire.

An inflation lumen, indicated at 132 in FIG. 6, is disposed parallel to central lumen 122, and is used for inflation and deflation of cuff 112. Inflation lumen 132 features substantially the same construction as inflation lumen 40 of FIG. 2 and passes through a side-arm port 134 (FIG. 5) connected to catheter 114. As shown in FIG. 5, side-arm port 134 also features a Luer-lock fitting 135 that accepts a standard syringe 137 so that inflation material 136 may be used to inflated cuff 112. A check-valve arrangement may be substituted for Luer-lock fitting 135.

A cuff-positioning string lumen, shown at 142 in FIG. 6, is disposed parallel to the other two lumina and extends along the opposite side of central lumen 122 from inflation lumen 132. As shown in FIG. 5, one end of cuff-positioning string lumen 142 terminates at the proximal end of syringe 114 in a standard syringe-compatible hub 144. Like ports 124 and 134, hub 144 remains external to the patient's body when the device is in use.

A small gauge filament, indicated at 152, features substantially the same construction as filament 42 of FIGS. 1 through 3. It extends the length of cuff-positioning string lumen 142 and emerges from hub 144 and opening 146, the latter of which is near cuff 112. Filament 152 exits opening 146 as a loop and is attached to the circumference of cuff 112 at point 154 which is the furthest distance from catheter 114.

Alternatively, filament 152 may be attached circumferentially through the inflation space of cuff 112.

The portion of filament 152 exiting hub 144, since it is external to the patient's body, may be manipulated by the operator. By applying tension to filament 152, and thus the filament loop attached to cuff 112, the orientation of cuff 112 may be altered within the blood vessel lumen as the cuff, in effect, pivots about the junction between cuff 112 and catheter 114. As such, the opening of cuff 112 and the opening of filter 116, can be positioned so as to be perpendicular to the axis of blood flow within the blood vessel. Futhermore, continued tension on filament 152 reduces the opening of cuff 112, and thus the opening of filter 116, in a purse-string fashion, especially when cuff 112 is deflated. This allows clot capture and entrapment within filter 116. A such, the clot may then be removed from the patient's body along with filter 116. In the absence of clots, tensioning of filament 152 collapses cuff 112 after it has been deflated using inflation lumen 132. This facilitates removal of catheter 114 from the blood vessel and the patient's body.

Figures 7A, 7B, 7C:
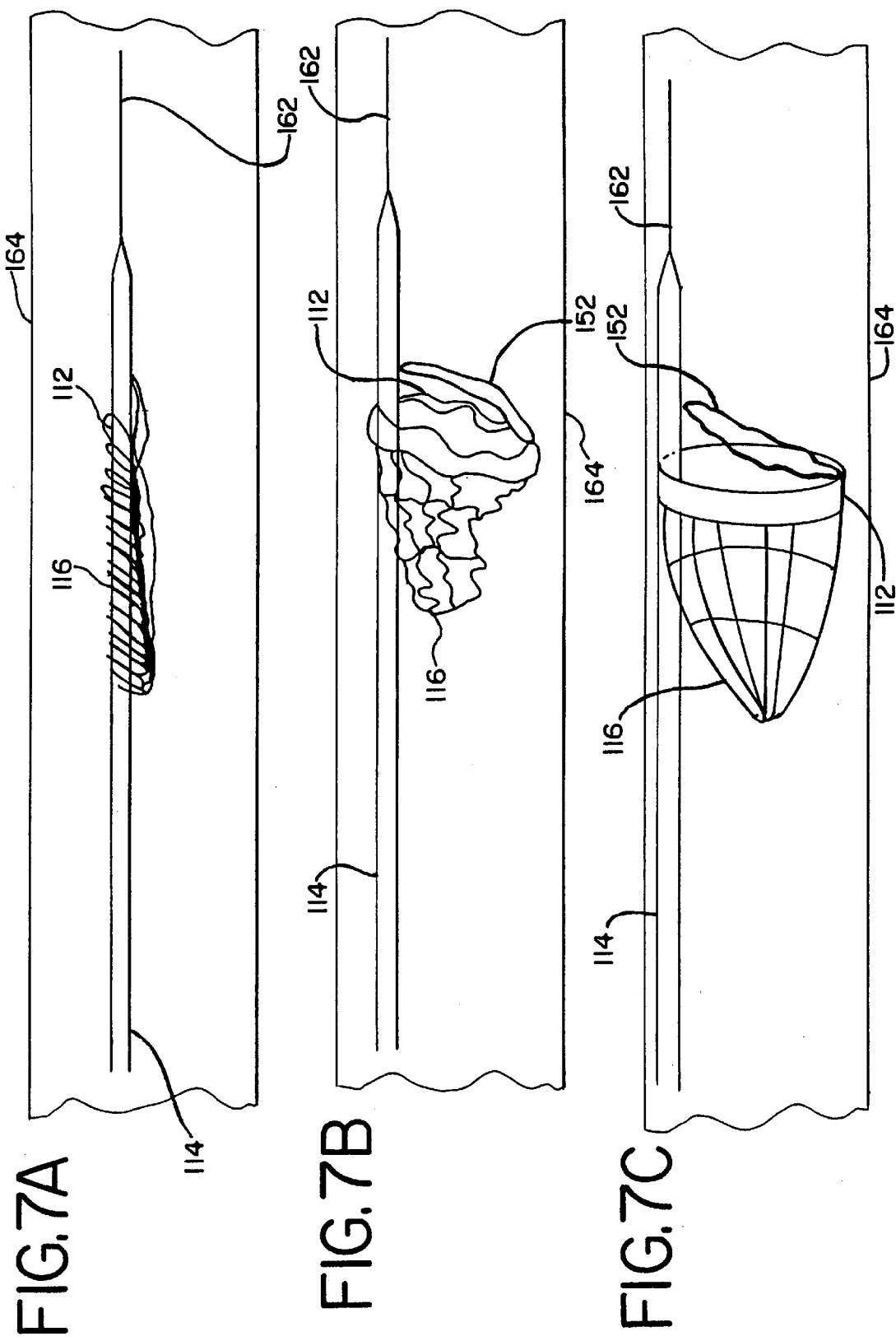
FIGS. 7A through 7C show in cross-section a blood vessel with a side elevation view of the vena cava filter device of FIG. 5 being deployed therein.

FIGS. 7A through 7C illustrate the steps to be performed in deploying the inflatable temporary vena cava filter device. Initially, catheter 114, with filter 116 and deflated cuff 112 wrapped around it, is loaded over a previously placed guidewire 162, via guidewire lumen 122, and is fed through the catheter insertion or access site. Preferred access sites include the jugular veins, the subclavian veins, and the femoral veins. The length of guidewire 162 is such that a sufficient portion of it emerges from the access site so as to allow the entire length of catheter 114 to be loaded onto guidewire 162, externally from the patient's body, with a portion of guidewire 162 remaining after port 124 (FIG. 5) for the operator to grip as catheter 114 is being advanced to its final position.

As shown in FIG. 7A, once catheter 114 is inserted through the venous access site, it is positioned at the desired point within inferior vena cava 164. Inflation material is then injected into cuff 112 via inflation lumen 132 (FIG. 6), as illustrated in FIG. 7B. After cuff 112 is fully inflated, as shown in FIG. 7C, the orientation of its opening and the opening of filter 116 may be adjusted via filament 152 as discussed above. The inflated cuff 112 is preferably disposed transversely within a vessel lumen, juxtaposed circumferentially to the interior wall of vena cava 164, although not necessarily contacting the wall. Catheter 114 remains in place with cuff 112 attached to hold filter 116 in position within inferior vena cava 164. When filtering is no longer required, or a blood clot has been captured within filter 116, cuff 112 may be deflated through inflation lumen 132 and collapsed via filament 152 for withdrawal from the patient's body along with catheter 114 via the access site.

While the preferred embodiments of the invention have been shown and described, it will be apparent to those skilled in the art that changes and modifications may be made therein without departing from the spirit of the invention, the scope of which is defined by the appended claims.

What is claimed is:

1. An apparatus for removing objects from tubular structures in the human body comprising:
    a) a catheter having a longitudinal axis, a proximal portion and a distal portion;
    b) said catheter having an inflation lumen extending longitudinally and at least partially therethrough with ports in the proximal and distal portions of the catheter;
    c) an inflatable cuff having an inflation space, said cuff permanently attached near the distal portion of said catheter, said inflation space being in communication with the distal inflation lumen port;
    d) means for inflating and deflating the cuff with inflation material;
    e) a pouch attached to the inflatable cuff for deployment when said cuffs inflated so that objects may be received within said pouch; and
    f) a filament disposed in the inflation space of the cuff, said filament having a portion extending out of the proximal portion of the catheter so that said cuff may be cinched and said pouch closed in a purse string fashion to capture objects within said pouch for removal from the human body.

2. The apparatus of claim 1 further comprising a central lumen extending through said catheter coaxially with the longitudinal axis of said catheter and having ports in the proximal and distal portions of the catheter so that said central lumen may slidingly receive a guidewire along which said catheter may travel.

3. The apparatus of claim 2 wherein the proximal port of the central lumen is adapted to receive a syringe so that a fluid may be injected through the central lumen and into the tubular structure.

4. The apparatus of claim 1 wherein said pouch is porous so that objects may be filtered from a fluid.

5. The apparatus of claim 1 wherein said pouch is non-porous.

6. The apparatus of claim 1 wherein the inflation lumen port in the proximal portion of the catheter is a side-arm port.

7. The apparatus of claim 1 wherein the inflation lumen port in the proximal portion of the catheter is adapted to receive a syringe and the means for inflating the cuff is the syringe.

8. The apparatus of claim 1 wherein the cuff includes an inner surface and said cuff is attached to the distal portion of said catheter by said inner surface.

9. The apparatus of claim 8 wherein said pouch features an aperture through which the distal portion of said catheter passes.

10. The apparatus of claim 1 wherein said cuff features an outer surface and is sized so that when it is inflated, said outer surface abuts the tubular structure.

11. An apparatus for removing objects from tubular structures in the human body comprising:
    a) a catheter having a longitudinal axis, a proximal portion and a distal portion;
    b) said catheter having an inflation lumen extending longitudinally and at least partially therethrough with ports in the proximal and distal portions of the catheter;
    c) an inflatable cuff having an inflation space, said cuff attached near the distal portion of said catheter, the inflation space of said cuff being in communication with the inflation lumen;
    d) means for inflating and deflating the cuff with inflation material via the proximal inflation lumen port;
    e) a pouch attached to the inflatable cuff for deployment when said cuff is inflated so that said objects may be received within said pouch; and
    f) a filament disposed within the inflation lumen and the inflation space of the cuff, said filament having a portion extending out of said proximal inflation lumen port of said catheter so that said cuff may be cinched and said pouch closed in a purse-string fashion to capture objects within said pouch for removal from the human body.

12. The apparatus of claim 11 further comprising a central lumen extending through said catheter coaxially with the longitudinal axis of said catheter and having ports in the proximal and distal portions of the catheter so that said central lumen may slidingly receive a guidewire along which said catheter may travel.

13. The apparatus of claim 12 wherein the proximal port of the central lumen is adapted to receive a syringe so that a fluid may be injected through the central lumen and into the tubular structure.

14. The apparatus of claim 11 wherein said pouch is porous so that objects may be filtered from a fluid.

15. The apparatus of claim 11 wherein said pouch is non-porous.

16. The apparatus of claim 11 wherein the inflation lumen port in the proximal portion of the catheter is a side-arm port.

17. The apparatus of claim 11 wherein the inflation lumen port in the proximal portion of the catheter is adapted to receive a syringe and the means for inflating the cuff is the syringe.

18. The apparatus of claim 11 wherein the cuff includes an inner surface and said cuff is attached to the distal portion of said catheter by said inner surface.

19. The apparatus of claim 18 wherein said pouch features an aperture through which the distal portion of said catheter passes.

20. The apparatus of claim 11 wherein said cuff features an outer surface and is sized so that when it is inflated, said outer surface abuts the tubular structure.

21. A method for removing objects from tubular structures in the human body comprising the steps of:

a) inserting a catheter with a collapsed, inflatable cuff into the tubular structure, said inflatable cuff having a pouch attached thereto;

b) inflating said cuff so that the pouch spans the tubular structure;

c) moving said catheter so that the object to be removed is received in said pouch;

d) deflating said cuff;

e) cinching said cuff so that said pouch is closed with the object to be removed captured inside; and f) withdrawing said catheter, cuff and pouch from the tubular structure.

22. The method of claim 21 further comprising the step of passing the catheter over a guidewire before it is inserted into the tubular structure.

* * * * *